United States Patent [19]

Avenia et al.

[11] 4,041,076
[45] Aug. 9, 1977

[54] IMMUNOASSAY FOR PHARMACOLOGICALLY ACTIVE PHENETHYLAMINES

[75] Inventors: Richard William Avenia, Nutley; James Gordon Christenson, North Caldwell; Benjamin Pecherer, Montclair, all of N.J.

[73] Assignee: Hoffmann-La Roche Inc., Nutley, N.J.

[21] Appl. No.: 665,205

[22] Filed: Mar. 9, 1976

Related U.S. Application Data

[62] Division of Ser. No. 517,267, Oct. 23, 1974, abandoned.

[51] Int. Cl.$^2$ ........................................... C07C 103/38
[52] U.S. Cl. .............................. 260/559 A; 23/230 B; 260/112 R; 260/112.5 R; 252/408; 424/1
[58] Field of Search ..................................... 260/559 A

[56] References Cited

FOREIGN PATENT DOCUMENTS 1,345,075    1/1974    United Kingdom

Primary Examiner—Arthur P. Demers
Attorney, Agent, or Firm—Samuel L. Welt; George M. Gould

[57] ABSTRACT

New hapten compositions useful in preparing antigens which may be employed in eliciting antibodies useful in an improved radioimmunoassay for pharmacologically active phenethylamines are disclosed. Particular phenethylamines which are preferably detected by the present radioimmunoassay include the catecholamines such as norepinephrine, dopamine and epinephrine, and the amphetamines.

2 Claims, No Drawings

IMMUNOASSAY FOR PHARMACOLOGICALLY ACTIVE PHENETHYLAMINES

This is a division of application Ser. No. 517,267 filed Oct. 23, 1974, now abandoned.

BACKGROUND OF THE INVENTION

A radioimmunoassay for catecholamines is described in U.S. Pat. No. 3,704,282. The antigen utilized for eliciting the needed catecholamine specific antibody was prepared by directly coupling the catecholamine to the protein or polypeptide immunogenic carrier using a carbodiimide coupling agent. The resulting antigen is formed by an amide bond linkage of the amine group of the catecholamine with pendant carboxy groups of the support materials. However, the antibody elicited by use of such antigens suffers from a lack of specificity with respect to the critical ethylamine side chain.

Faraj et al., in a paper appearing Pharmacologist, June 1974, describe the preparation of an antibody specific to tyramine. The antigen used for eliciting this antibody is prepared by coupling p-aminohippuric acid to methylated bovine serum albumin followed by diazotization of the amino group and reaction of the diazonium intermediate with tyramine. U.S. Pat. No. 3,690,834 teaches the preparation of antigens and antibodies to a large number of biologically active compounds. The antigens are prepared by linking the compounds to a protein carrier through a suitable linkage. These antigens may then be used to elicit antibodies by conventional procedures. The antibodies and spin-labeled derivatives of the biologically active compounds are then used in an assay procedure. One of the class of active compounds disclosed is the amphetamines (column 9, line 54 to column 10, line 4.

DESCRIPTION OF THE INVENTION

The present invention relates to an improved radioimmunoassay for detection of phenethylamine compounds of the following formula:

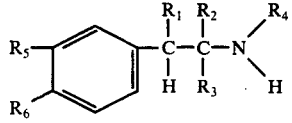

I wherein $R_1$ is hydrogen or hydroxy; $R_2$ is hydrogen or lower alkyl; $R_3$ is hydrogen or lower alkyl; $R_4$ is hydrogen, lower alkyl, phenoxy lower alkyl and phenyl lower alkyl; $R_5$ is hydrogen, trifluoromethyl, hydroxy or lower alkoxy; and $R_6$ is hydrogen, hydroxy, halogen, or lower alkoxy. In particular the instant invention relates to new haptenic compounds of the formula:

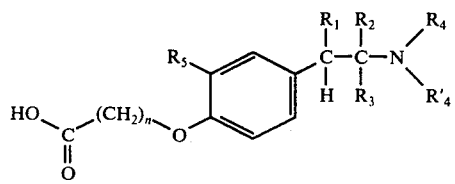

II wherein $R_1$, $R_2$, $R_3$, $R_4$ and $R_5$ are as above, $R'_4$ is hydrogen or a conventional amine protecting group and $n$ is an integer from 1 to 3.

Preferred compounds for use in the practice of the present invention are obtained when $R_1$ is hydrogen or hydroxy, $R_2$ is hydrogen or methyl, $R_3$ is hydrogen, $R_4$ is hydrogen or methyl, $R'_4$ is t-butoxycarbonyl, $R_5$ is hydrogen or hydroxy and $n$ is 1.

The t-butoxycarbonyl group is employed as a protective group in compounds of formula II to serve to prevent self-condensation reactions during further transformations in the preparation of the needed antigens. The t-butoxycarbonyl group can be readily cleaved to yield an antigen wherein $R'_4$ is hydrogen.

In order to prepare the antigens needed in the present invention, it is necessary that the hapten of formula II be covalently bonded through the carboxylic group to a conventional immunogenic carrier material. As used herein, the term "immunogenic carrier material" is meant to include those materials which have the property of independently eliciting an immunogenic response in a host animal and which can be covalently coupled to the above described haptens. Suitable carrier materials include for example, proteins; natural or synthetic polymeric compounds such as polypeptides, e.g., polylysine or copolymers of amino acids; polysaccharides; and the like. Particularly preferred carrier materials are proteins and polypeptides, especially proteins.

The identity of the protein material utilized in the preparation of an antigen of the instant invention is not critical. Examples of suitable proteins useful in the practice of this invention include mammalian serum proteins such as, for example, human gamma globulin, human serum albumin, bovine serum albumin, methylated bovine serum albumin, rabbit serum albumin and bovine gamma globulin. Other suitable protein products will be suggested to one skilled in the art. It is generally preferred but not necessary that proteins be utilized which are foreign to the animal hosts in which the resulting antigen will be employed.

The covalent coupling of the hapten to the immunogenic carrier material can be carried out in a manner well known in the art for establishing amide bonds. However, to ensure an adequate degree of coupling under the mildest possible conditions so as to minimize any possible deleterious effect on the carrier material it may be desirable to convert the hapten of formula II to an isolatable activated form prior to coupling. One particularly preferred isolatable activated form is the N-hydroxysuccinimide ester as indicated by formula III

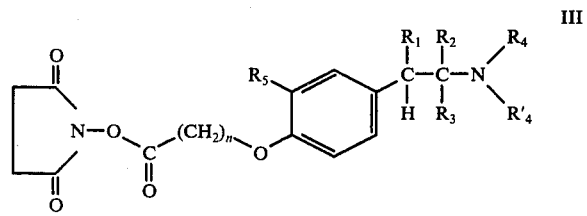

III wherein $R_1$, $R_2$, $R_3$, $R_4$, $R'_4$, $R_5$ and $n$ are as above.

Other suitable isolatable activated derivatives include the p-nitrophenyl esters; acylimidazoles; and so forth. Other methods for coupling may be employed wherein the activated intermediates need not be isolated. Such methods include the mixed anhydride method, use of EEDQ (N-ethoxycarbonyl-2-ethoxy-1,2-dihydroquinoline) as coupling agent and the like.

The coupling of the hapten either as the free acid of formula II or more preferably as an activated derivative, e.g., formula III, to the immunogenic carrier material can be readily accomplished utilizing techniques now well known in the art for establishing amide bonds. Thus, for example, one such technique would involve dissolving the carrier material and a coupling agent in a suitable inert solvent followed by adding the desired hapten of formula II. The reaction may be conducted in a temperature in the range of from about 0° C. to about 50° C. although higher or lower temperatures might be employed depending on the nature of the reactants. A most preferable temperature is about room temperature.

The coupling agent which may be used in the aforesaid reaction will be selected from those commonly employed in organic chemistry for initiating amide bond formation. A particularly suitable group of coupling agents comprise the carbodiimides, most preferably dicyclohexylcarbodiimide or 1-ethyl-3-(3-dimethylaminopropyl)carbodiimide. The molar ratio of the hapten to the carrier material will, of course, depend on the identity of the hapten utilized and the protein selected for the reaction.

Conventional conditions for the coupling reaction can be employed. Thus when utilizing carbodiimides as coupling agents, it is desirable to utilize a slightly acidic reaction medium for this step, e.g., a medium having a pH in the range of from about 3 to 6.5, most preferably in the range of from about 4 to 6.5. Upon completion of the reaction, the excess hapten molecules may be removed by dialysis.

As indicated previously, one preferred technique for preparing the antigens of the present invention is to first prepare and isolate an activated derivative, i.e., a compound of formula III, and then to react this compound with the carrier material to form the block antigen. Such activated derivatives are conveniently prepared by reacting a compound of formula II with a desired activating compound, such as N-hydroxysuccinimide, and a coupling agent, such as dicyclohexylcarbodiimide, in an inert solvent. The reaction is usually allowed to proceed for 16–60 hours at reduced temperatures (0°–5° C.). The activated derivative may then be isolated by filtering off the by-product, dicyclohexylurea, and distilling off the solvent.

The hapten may then be coupled to the carrier material by contacting the activated derivative with the chosen carrier material. When the activated derivative is the N-hydroxysuccinimide ester and the carrier material is bovine serum albumin, this may be accomplished by adding the activated derivative in a water-miscible solvent to an aqueous solution of the carrier material containing a base, such as sodium bicarbonate.

Another method of coupling carrier protein to hapten (formula II) is by activating the carboxyl group of the hapten without isolation of an intermediate and adding the activated hapten to the carrier protein. An example of such a reaction is the mixed anhydride obtained by reaction with isobutylchloroformate. The hapten is dissolved in an anhydrous, water-miscible organic solvent, usually dioxane, and the solution is neutralized with an equimolar quantity of triethylamine. After stirring at room temperature, the temperature of the mixture is reduced to between 0° and 8° C. An equimolar quantity plus 10% excess of isobutylchloroformate is then added and stirring is continued. Meanwhile, the carrier protein, e.g., bovine serum albumin, is dissolved in water and the pH is adjusted to 9.0 with NaOH. The quantity of carrier used is equivalent to the molar quantity of hapten divided by the theoretical number of reactive groups on the carrier. Organic solvent is added to the carrier solution and the solution is cooled to between 0° and 8° C. The solution is then added to the activated hapten and coupling is allowed to proceed for 30 minutes to overnight. The final ratio of organic solvent to water is 1:1.

The mixture is then adjusted to neutrality, the aqueous-organic solvent is removed and aqueous solution is effected. After dialysis and lyophilization, the amine-protecting group is removed.

Following coupling of a compound of either formula II or formula III to the carrier material, it is necessary to remove the protective group ($R_4'$ in formulas II and III), in order to restore the free primary or secondary amino function. In the case of the t-butoxycarbonyl protective group, this may be conveniently achieved by treating the material with trifluoroacetic in dichloromethane at room temperature. The relative amounts of trifluoroacetic acid and dichloromethane and the time duration of the treatment may be varied to suit particular cases. In general, from one to three volumes of dichloromethane per volume of trifluoroacetic acid and reaction times of 30 to 60 minutes have been found to give good results.

The antigens of the present invention may be utilized to induce formation of antibodies specific to compounds of formula I above in host animals by injecting the antigen in such a host, preferably using an adjuvant. Improved titers can be obtained by repeated injections over a period of time. Suitable host animals for this purpose include mammals such as rabbits, horses, goats, guinea pigs, rats cows, sheep etc. The resulting antisera will contain antibodies which will selectively complex with the phenethylamines of formula I, formula II or an antigen prepared therefrom, as described above.

The specific antibodies of the present invention are useful as reagents for the determination of phenethylamines of formula I. In such an assay, a known amount of labelled phenethylamine is mixed with the above antibody and a sample containing some phenethylamine is added. The amount of phenethylamine in the sample can be determined by measuring the inhibition of the binding to the specific antibody of the labelled phenethylamine by the unknown sample. The reagents may be added in any order. A suitable assay procedure for this purpose is described in greater detail in U.S. Pat. No. 3,709,868.

Suitable labeled phenethylamines for assay purposes include radioisotopically labeled phenethylamines, particularly those labeled with tritium ($^3H$), carbon 14 ($^{14}C$) or with iodine 125 ($^{125}I$). One may also employ phenethylamines labeled with any other unique and detectable label such as for example an electron spin resonance group. Examples of the use of various electron spin resonance labeled molecules in bioassays are to be found in U.S. Pat. Nos. 3,453,288, 3,481,952 and 3,507,876. Other suitable labels include chromophores, fluorophors, enzymes, red blood cells, latex particles, etc.

The novel antigens and antibodies of the present invention may be utilized in conjunction with conventional additives, buffers, stabilizers, diluents, or in combination with other physiologically active substances. The preparation and use of compositions containing antigens or antibodies in conjunction with physiologically acceptable adjuvants is now known in the art.

The preparation of haptens of formula II can readily be accomplished starting from a corresponding phenethylamine compound having a free hydroxy group in the para position. In one such process aspect the 4-hydroxy phenethylamine derivative such as rac. 4-hydroxy-alpha-methylphenethylamine, is N,O-diacylated by reaction with an acylating agent, preferably acetic anhydride. The diacyl compound is then selectively saponified with strong base such as sodium hydroxide to yield the N-acyl compound. This product is then reacted successively with sodium hydride and a reagent of the formula X—(CH$_2$)$_n$—COOR where $n$ is as above, X is chloro or bromo and R is C$_{1-7}$ alkyl.

The N-acyl group and the ester group of the resulting phenoxyacetic ester are cleaved simultaneously in refluxing caustic solution. Thereafter the free amino group is reacted with a conventional amine protecting agent such as t-butoxycarbonyl azide. Finally, if desired the carboxyl group is activated by the formation of an active ester such as the N-hydroxysuccinimide ester of formula III.

In an alternative sequence the 4-hydroxyphenethylamine is converted first to the N-t-butoxycarbonyl derivative as above. This derivative is then reacted with the reagent X—(CH$_2$)$_n$—COOR. The ester on the linking group is saponified as above with base and the resulting free acid to converted to the activated ester, e.g., the N-hydroxysuccinimide ester as before.

These reaction sequences as well as other aspects of the present invention are further illustrated in the examples. It is understood that the intermediates employed in preparing the antigens of the invention include novel compounds, which novel compounds are included within the scope of the invention.

As used herein the term "lower alkyl" represents straight or branched chain hydrocarbon radicals containing from 1 to 7, preferably 1 to 4 carbon atoms, such as methyl, ethyl, i-propyl, t-butyl and the like. Lower alkoxy includes radicals of 1 to 7 carbon atoms such as methoxy, ethoxy, t-butoxy and the like. "Phenyl lower alkyl" includes groups such as benzyl and phenethyl. The term "halogen" is meant to include chlorine, bromine, iodine and fluorine. Conventional amine protecting groups include those of the acyl type (e.g., formyl, benzoyl, phthalyl, trifluoroacetyl, p-tosyl, aryl- and alkylphosphoryl, phenyl- and benzylsulfonyl, tritylsulfenyl, o-nitrophenylsulfenyl, -chlorobutyryl and o-nitrophenoxyacetyl), of the alkyl type (e.g., trityl, benzyl and alkylidene) and of the urethane type (e.g., carbobenzoxy, p-bromo-, p-chloro- and p-methoxycarbobenzoxy, tosyloxyalkyloxy-, cyclopentyloxy-, cyclohexyloxy-, t-butyloxy, 1,1-dimethylpropyloxy, 2-(p-biphenyl)-2-propyloxy- and benzylthiocarbonyl).

EXAMPLE 1 rac. N-(4-Acetoxy-alpha-methylphenethyl)acetamide

In a 1-l. flash, flushed with nitrogen and provided with a stirrer, thermometer, two dropping funnels, and a nitrogen inlet tube was placed a solution of 46.4 g. (0.2 moles) of rac. 4-hydroxy-alpha-methylphenethylamine hydrobromide in 100 ml. of water. The flask was cooled in an ice bath, and when the temperature reached 5° C, 40 ml. of acetic anhydride (0.395 moles) and 440 ml. of 2N NaOH were added simultaneously from the two dropping funnels at approximately equivalent rates, maintaining the temperature below 5° C. An oil gradually separated during the addition, and the mixture was stirred for another 4 hours at 5° C, then allowed to come to room temperature overnight. The oil that had solidified to a mass of crystals was recovered by filtration. After washing with water the solid was dried in vacuo over KOH and CaCl$_2$. Yield, 32 g. of mp. 92°–93.5°. An analytical sample was obtained by recrystallization from ethyl acetate —30°-60° C. petroleum ether; mp. 97.5° - 99° C.

Microanalysis: C, 66.19; H, 7.26; N, 6.01.

Calc for C$_{13}$H$_{17}$NO$_3$ (235.26): C, 66.36; H, 7.28; N, 5.95.

Their spectrum confirmed the presence of two acetyl groups.

EXAMPLE 2

N-(4-Hydroxy-alpha-methylphenethyl)acetamide

A 0.2 mole preparation of rac. N-(4-acetoxy-alpha-methylphenethyl)acetamide was prepared as described above except that a more concentrated sodium hydroxide solution was used: i.e., 16 g. of NaOH in 50 ml. of water. Overnight, the oil partially crystallized. The mixture was warmed to 60°-70° C. and 110 ml. of 10% NaOH solution added in portions until a permanent pH of 9 was obtained. The mixture was cooled to 25° C., 125 ml. of n-butanol was added; the two phase mixture transferred to a separatory funnel, and the layers separated. Three more extractions with n-butanol were made and the combined extracts dried with anhydrous MgSO$_4$. After removal of the drying agent by filtration, the solvent was distilled in a rotary evaporator. The traces of n-butanol that remained were removed by the addition of 100 ml. of water and reevaporation in a rotary evaporator, whereupon the residue crystallized on cooling; yield 46 g. The product was recrystallized from 450 ml. of boiling water and 26 g. of crystalline material, m.p. 154.4–158.5° was obtained. An analytical sample was obtained by recrystallization from hot ethyl acetate, m.p. 160.5°–163.5°.

EXAMPLE 3

Ethyl ester of rac. 4-(2-acetamidopropyl)phenoxy acetic acid

Twenty-six g. (0.135 moles) of N-(4-hydroxy-alpha-methylphenethyl) acetamide was dissolved in 400 ml. of hexamethylphosphoric triamide under nitrogen in a 1-l., three-necked flask provided with a stirrer, thermometer, inlet tube for nitrogen and dropping funnel. To this solution, 4.0 g. of sodium hydride (0.167 moles) was added at T <20°, and the mixture was stirred until hydrogen evolution had substantially ceased. To this solution of the sodium salt, 25.1 g. (0.15 moles) of ethyl bromoacetate dissolved in 25 ml. of benzene was added as rapidly as possible; the temperature quickly climbed from 19° to 36° and then began to drop. Athis point the mixture remained overnight at ambient temperature. The next morning the mixture was cautiously decomposed by the addition of 400 ml. of ice water and the oil that separated was recovered by four 200-ml. extractions with ether. The combined extracts were washed several times with small portions of cold water then dried over MgSO$_4$. The drying agent was removed by filtration and the filter cake washed with several portions of chloroform to remove any product that may have precipitated therewith. Distillation of the combined chloroform and ether filtrates in a rotary evaporator left a residue of 29 g. of an amber oil (77%) that crystallized on cooling. The oil was observed to melt at 70°–75° but was not further characterized.

EXAMPLE 4 rac. 4-(2-Aminopropyl)phenoxyacetic acid

The 29 g. of residual oil described in Example 3 above ethyl ester of rac. 4-(2-acetamidopropyl) phenoxy acetic acid was refluxed with 16.4 g. of sodium hydroxide 0.41 moles) in 150 ml. of water for 15 hrs., after which he solution was cooled, a trace of flocculent matter emoved by filtration and the clear filtrate passed over column of 750 ml. (0.75 eq) of Dowex 2-X4 in the ydrogen form. After washing the column with water ntil the effluent pH was 4–5, the amino acid was eluted vith 2 l of 10% aqueous pyridine. Distillation of the yridine effluent in a rotary evaporator left a residue of 8 g., m.p. 301°–303° dec.

A sample was recrystallized from water after which he m.p. was 303°–307° dec.

Microanalysis: C, 62.95; H, 7.28; N, 6.61.

Calc. for $C_{13}H_{14}NO_3$ (209.25): C, 63.14; H, 7.23; N, .69.

EXAMPLE 5 rac. 4-[2-(N-t-butoxycarbonamido)propyl]phenoxyacetic acid

To a suspension of 7.2 g. of magnesium oxide (0.18 ioles) in 300 ml. of water was added 12.54 g. of rac. -(2-aminopropyl)phenoxyacetic acid and the mixture irred for 1 hour after which 18.0 g. of t-butoxycarbonyl azide (0.126 moles) in 300 ml. of dioxane was added. he suspension was stirred at 50° for 18 hours, after hich time a pale amber suspension resulted. The dioxne was removed by distillation in the rotary evaporar, and the cooled aqueous residue brought to pH 3 by e dropwise addition of 10% citric acid solution. Exaction of the aqueous solution with five 75-ml. porons of chloroform removed the acid, and the comined extracts were washed twice with small portions of ater. The extract was dried over MgSO$_4$, the drying ent removed, and the solvent was distilled in the tary evaporator. A white crystalline residue, 16.3 g. f m.p. 142.5°–145.5° remained. A small second crop, 46 g. of the same m.p. was obtained from the MgSO$_4$ lter cake.

A sample was recrystallized from toluene after which e m.p. was 143°–144.5°.

Microanalysis: C, 62.12; H, 7.49; N, 4.53.

Calc. for $C_{16}H_{23}NO_5$ (309.36): C, 62.12; H, 7.44; N, 46.

EXAMPLE 6 t-Butyl ester of rac. N-(4-hydroxy-alpha-methylphenethyl)carbamic acid

In a 1-l., three neck, r.b. flask equipped with a stirrer, ermometer, and gas inlet tube for nitrogen were aced 46.42 g. of rac. 4-hydroxy-alpha-methylenethyl amine hydrobromide (0.2 mole), 300 ml. of ater, 300 ml. of dioxane, 12 g. of magnesium oxide (0.3 ole) and 43 g. of t-butoxycarbonylazide (0.3 mole) he mixture was stirred at 40°–45° for 18 hours. The oled, pale amber, turbid solution was brought from 1 8 to pH 5 by addition of a few ml. of acetic acid and e dioxane distilled in a rotary evaporator. To the sulting mixture of two liquid phases, 500 ml. of water as added and the organic phase collected by five 100- l. extractions with n-butanol. The combined extracts ere washed with two small portions of water, then dried over MgSO$_4$. After removal of the drying agent, the solvent was distilled in a rotary evaporator. The last traces of n-butanol were removed by the addition of 150 ml. of toluene and distillation in the rotary evaporator, finally at a pot temperature of 75°. The residue, 51 g. crystallized under petroleum ether, mp. 93°–95.5°. This was dissolved in 350 ml. of 60°–90° petroleum ether and 150 ml. of ethyl acetate, treated with a little Alox, filtered, and to the warm filtrate, 450 ml. of 60°–90° petroleum ether was added. After cooling to room temperature the mixture was chilled in an ice bath for 4 hours, the crystalline product collected by filtration, washed with a little 60°–90° petroleum ether and dried. Yield 32.6 g. (65%), m.p. 98.5°–101.5°.

Microanalysis: C, 67.14; H, 8.54; N, 5.55.

Calc. for $C_{14}H_{21}NO_3$ (251.32): C, 66.91; H, 8.42; N, 5.57).

The mother liquor was stripped of solvent and covered with 100 ml. of 60°–90° petroleum ether plus a few ml. of ethyl acetate. After chilling for several hours, another 3 g. of product, m.p. 97.5°–100°, was obtained; this was also used in the next stage.

EXAMPLE 7

Ethyl ester of rac. 4-(2-t-butoxycarbonamidopropyl)phenoxyacetic acid

Thirty-two g. of the above described rac. N-(4-hydroxy-alpha-methylphenethyl) carbamic acid t-butyl ester (0.127 moles) was dissolved in 350 ml. of hexamethylphosphoric triamide in a 1-l., r.b. -flask provided with a stirrer, thermometer, and inlet tube for nitrogen. To this solution, cooled to 0°–2°, was added the sodium hydride obtained by washing 6.1 g. of the 57% dispersion in mineral oil (0.144 moles) three times with pentane. After 2 hours, hydrogen evolution became very slow, and a thick paste of the sodium salt resulted. To this suspension, 21.5 g. of ethyl bromacetate (0.128 moles) in 25 ml. of benzene was added at once; the mixture began to thin out immediately with only a slight rise in temperature (2°). The mixture was stirred for 2 hours at 0°–2°, then allowed to stand at room temperature for 12 hours. To the clear amber solution, 750 ml. of ice and water was added, and the oil that separated was collected by five extractions with 125-ml. portions of ether. The combined extracts were freed of traces of the triamide by several small washes with water. After drying over MgSO$_4$ and distillation of the solvent, there remained 43 g. of pale amber oil. One g. of this oil was distilled in a "Bantam-Ware" short path still and but for a small forerun (solvent) the entire pot contents distilled as a very pale colored viscous oil at 163°–166°/0.03 mm.

Microanalysis: C, 64.14; H, 8.13; N, 4.40.

Calc. for $C_{18}H_{27}NO_5$ (337.43): C, 64.08; H, 8.07; N, 4.15.

EXAMPLE 8 rac. 4-(2-t-Butoxycarbonamidopropyl)phenoxyacetic acid 41 g. of the above undistilled ester, ethyl ester of rac. 4-(2-t-butoxycarbonamidopropyl)phenoxyacetic acid, was heated on a steam bath with 100 ml. of water and to the stirred solution 10% sodium hydroxide was added until a permanent pH of 9 was obtained. At this point the hydrolysate remained at room temperature overnight. After four extractions was 50-ml. portions of chloroform to remove neutral material, the solution was cooled to 10°, and brought to pH 3 by the addition of 25% citric acid. An oil separated that soon solidified. The oil was dissolved by the addition of 1800 ml. of chloroform, the aqueous layer separated, and the chloroform solution washed twice with small portions of water and dried. After removal of the drying agent distillation of the solvent, there remained 35.5 g. of a white solid, m.p. 137°-139° dec. This solid was dissolved in 1 l of hot toluene and allowed to crystallize overnight at room temperature. The product, after drying, first at 65° in vacuo, and then at 100°, weighed 29.1 g. m.p. 144.5°-146.5°.

EXAMPLE 9

N-Hydroxysuccinimide ester of rac. 4-(2t-butoxycarbonamidopropyl)phenoxyacetic acid To a chilled solution of 15.47 g. (0.05 moles) of rac. 4-(-2-t-butoxycarbonamidopropyl)phenoxyacetic acid and 6.5 g. (0.057 moles) of N-hydroxysuccinimide in 250 ml. of ethyleneglycol dimethyl ether was added a solution of 11.33 g. (0.055 moles) of dicyclohexylcarbodiimide in 100 ml. of ethyleneglycol dimethyl ether. Within a few minutes the solution began to deposit dicyclohexylurea. This mixture was refrigerated for 60 hours at 4°, then the dicyclohexylurea was removed by filtration and the solvent distilled from the filtrate in a rotary evaporator. The residue weighed 21.1 g, m.p. 143.5°-145.5° and recrystallized from 350 ml. of 2-propanol. After chilling in an ice bath for 6 hours, 18 g. of crystalline solid was recovered, m.p. 149°-151.5°.

Microanalysis: C, 59.07; H, 6.64; N, 6.70.

Calc. for $C_{20}H_{26}N_2O_7$ (406.44): C, 59.10; H, 6.45; N, 6.89.

EXAMPLE 10

Preparation of Immunogen (Bovine Serum Albumin Conjugate of rac. 4-(2-aminopropyl)phenoxyacetic acid Bovine serum albumin (BSA) (300 mg.) was dissolved in 12 ml. of water and 6 ml. of 0.5 M sodium bicarbonate was added. The N-hydroxysuccinimide ester (61 mg.) was dissolved in 6 ml. of dimethoxyethane and added dropwise to the BSA solution with stirring. The solution was stirred for 4 hours at room temperature, then allowed to stand at 4° overnight. The solution was then diluted to approximately 50 ml. with water and concentrated by ultrafiltration (Amicon PM-10 membrane) to 5-10 ml. This dilution and concentration procedure was carried out at least four times, or until the $A_{260}$ of the filtrate had decreased from approximately 25 to less than 0.2. The final concentrate was dialyzed overnight at 4° against 1 liter of water. The dialysate was changed and dialysis repeated twice for about 4 hours each time. The solution was then lyophilized. The lyophilized material was redissolved in 10 ml. of trifluoroacetic acid/dichloromethane (1/1, v/v) and allowed to stand for at least 30 min. in the dark at room temperature. The purple solution was then evaporated to dryness under a stream of nitrogen. The purple residue was resuspended in 20 ml. of water and brought to pH 6-9 with 1N sodium hydroxide. The resulting clear, colorless solution was dialyzed against one liter of phosphate buffered saline (0.9%NaCl in 0.005 M sodium phosphate, pH 7.2) overnight at 4°. The dialysate was changed and dialysis continued for 4 hr.

The degree of incorporation of hapten in two immunogen preparations was estimated at 30-50 moles of hapten per mole of BSA by radioimmunoassay. The molecular weight of the immunogen from one preparation was estimated by electrophoresis on a gradient polyacrylamide gel slab in the presence of sodium dodecyl sulfate. The average electrophoretic mobility of the immunogen was slightly less than that of BSA and corresponded to a molecular weight of about 72,000, indicating incorporation of approximately 20 moles of hapten per mole of BSA, in reasonable agreement with the results of radioimmunoassay.

EXAMPLE 11

Immunization and Bleeding

For immunization of goats, the dialyzed material of Example 10 was diluted with phosphate buffered saline to an $A_{274}$ of approximately 1.0. The diluted immunogen was then emulsified with an equal volume of Freund's adjuvant. The first three inoculations (using complete adjuvant) were administered at weekly intervals, the fourth after another 3 weeks, and monthly thereafter (the fourth and successive inoculations used incomplete adjuvant). Each inoculation comprised two subcutaneous injections of 0.5 ml. each.

Test bleedings were taken 2, 3, and 4 weeks after the first inoculation. After 5 weeks, and at biweekly intervals thereafter, 300 ml. of blood was drawn and serum prepared by standard techniques.

Preparation of Labeled rac. 4-hydroxy-alpha-methylphenethylamine hydrobromide

The radioactive amphetamine analog was prepared by iodination with $^{125}I$ using techniques known per se, using $Na^{125}I$ and chloramine-T. The substrate for iodination was rac. 4-hydroxy-alpha-methylphenethylamine hydrobromide (2 mg/ml. in 0.05 M sodium borate, pH 8.5).

Assay Procedure

The assay procedure is similar to that used in the Abuscreen™ radioimmunoassay for morphine. The sample volume required for the assay is 0.1 ml. For quantitative evaluation, standard curves are prepared on semilogarithmic paper using 10, 2, 1, 0.5, 0.25, 0.125 and 0.0625 μg of d-amphetamine per ml. of normal human urine.

Performance of the Assay

Amphetamine standards were prepared by diluting a 1.363 mg/ml. aqueous solution of d-amphetamine sulfate (1.000 mg/ml. of amphetamine as free base) to the required concentration with normal human urine. The assay can readily detect amphetamine levels on the order of 0.1 μg of amphetamine in 0.1 ml. of urine.

Further, as indicated by the results summarized in Table 1, the test is highly specific for amphetamines. Even compounds which are very closely related to amphetamine in structure, such as phenylpropanolamine and phentermine show only a small fraction of the activity of amphetamine. It should be pointed out, however, that these data were obtained using pooled antisera which were selected for low cross-reactivity. Antisera giving a positive test (equal to or greater than the equivalent of 1μg/ml. of amphetamine) with any of the tested compounds at 10 μg/ml were not included in this pool. The cross-reactivity of phentermine is particularly high and common to many sera. Individual sera yielding the equivalent of 2-5 μg/ml. of amphetamine when tested with 10 μg/ml. of phentermine are not unusual.

In Table 2, the cross-reactivity of various compounds in the radioimmunoassay is compared with those found by two other immunoassays, the Free Radical Assay Technique (FRAT) and the Enzyme Multiplied Immunoassay Technique (EMIT). The radioimmunoassay is clearly superior in all cases which can be compared.

Table 1

CROSS-REACTIVITIES OF VARIOUS AMPHETAMINE-LIKE COMPOUNDS IN RADIOIMMUNOASSAY FOR AMPHETAMINE

| Compound | Structure | Cross-reactivity(1) |
|---|---|---|
| Phenmetrazine | 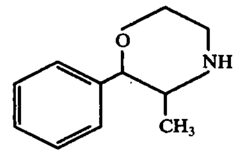 | 0.06 |
| Dextromethorphan | 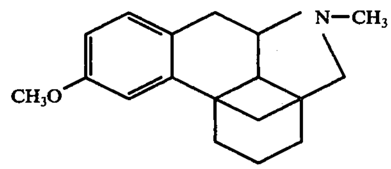 | 0.003 |
| Phenylpropanolamine | 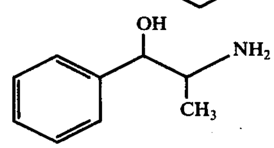 | 0.17 |
| Propylhexedrine | 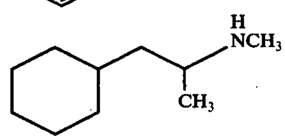 | 0.3 |
| Phentermine | 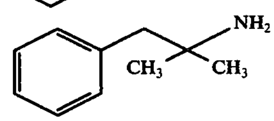 | 0.7 |
| Ephedrine (1-form) | 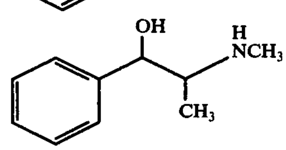 | 0.003 |
| Isoproterenol | 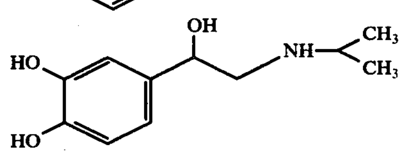 | 0 |
| Tyramine | 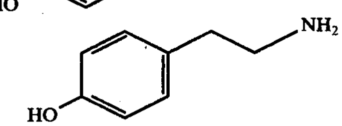 | 0.17 |
| Norepinephrine | 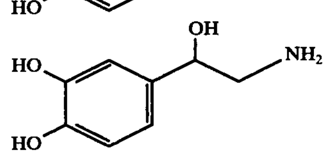 | 0.003 |
| Dopamine | 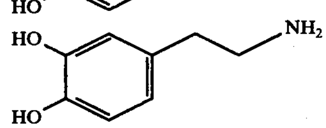 | 0.015 |

(1) Cross-reactivity is defined as the concentration (in μg/ml.) of amphetamine equivalent in the assay to 10 μg/ml. of the test drug. Thus, for example, a test solution of 10 μg/ml. of tyramine was found to displace from the antibody as much $^{125}$I as a solution of 0.17 μg/ml. of amphetamine.

Table 2

CROSS-REACTIVITIES OF VARIOUS DRUGS IN IMMUNOASSAY TECHNIQUES

| Compound | Structure (if not shown in Table 1) | Relative Reactivity* | | |
|---|---|---|---|---|
| | | FRAT$^R$** | EMIT$^R$** | Radioimmunoassay |
| Ephedrine | | 0.15 | 0.2 | 0.0003 |

Table 2-continued
CROSS-REACTIVITIES OF VARIOUS DRUGS IN IMMUNOASSAY TECHNIQUES

| Compound | Structure (if not shown in Table 1) | Relative Reactivity* FRAT[R]** | EMIT[R]** | Radioimmunoassay |
|---|---|---|---|---|
| Isoxsuprine | [structure: HO-C6H4-CH(OH)-CH(CH3)-NH-CH(CH3)-CH2-O-C6H5] | 0.05 | 0.2 | 0 |
| Nylidrin | [structure: HO-C6H4-CH(OH)-CH(CH3)-NH-CH(CH3)-CH2-CH2-C6H5] | 0.1 | — | — |
| Phentermine | | 1.0 | — | 0.07 |
| Propylhexedrine | | 0.5 | — | 0.03 |
| Cyclopentamine | [structure: thiolane-CH2-CH(CH3)-NHCH3] | 0.2 | 0.3 | 0.02 |
| Mephentermine | [structure: C6H5-CH2-C(CH3)2-NHCH3] | — | 0.6 | — |

**FRAT[R] and EMIT[R] data were obtained from W. J. Braitin and I. Sunshine, Am. J. Med. Technol. 39, 223 (1973).
*Note that, in this table, cross-reacitvity is expressed as "relative reactivity".

EXAMPLE 12 t-Butyl ester of N-(4-hydroxyphenethyl) carbamic acid 25 g. of tyramine (0.183 moles) and 35 g. of t-butoxy carbonylazide (0.25 moles) were stirred together in a mixture of 300 ml. of dioxane, 300 ml. of water, and 4 g. of magnesium oxide (0.1 mole) at 37°–45° C., for 21 hours under nitrogen. The dioxane was distilled from the deep amber solution in the rotary evaporator. After adjusting to pH to 6 with a little acetic acid, the solution was extracted five times with 200-ml. portions of chloroform. The combined chloroform extracts were washed with a little water, the solution dried, then the solvent distilled leaving a syrupy residue that soon crystallized. Yield 44 g. of a somewhat tacky solid. A sample was recrystallized from ethyl acetate — 60°–90° petroleum ether, after which the m.p. was 73.5°–76.5° C.

Microanalysis: C, 65.96; H, 8.39; N, 5.75.
Calc. for $C_{13}H_{19}NO_3$: C, 65.80; H, 8.07; N, 5.90.

EXAMPLE 13 t-Butyl ester of rac. N-(4,alpha-dihydroxyphenethyl) carbamic acid

In the same manner as described in Example 12 there was obtained from 47.5 g. of rac. octopamine hydrochloride (0.25 moles), 53.6 g. of t-butoxycarbonyl azide (0.375 moles) and 12 g. of magnesium oxide (0.30 moles) in 1 liter of 50% aqueous dioxane, 59.0 g. of crystalline solid, of m.p. 146°–148° C. After recrystallization from a mixture of ethyl acetate and 60°–90° petroleum ether, the product melted at 147°–148° C.

Microanalysis: C, 61.71; H, 7.70; N, 5.47.
Calc. for $C_{13}H_{19}NO_4$: C, 61.65; H, 7.56; N, 5.33.

EXAMPLE 14 t-Butyl ester of rac. N-(4, alpha-dihydroxyphenethyl)-N-methyl carbamic acid 41.8 g. (0.28 moles) of rac. synephrine and 53.6 g. (0.375 moles) of t-butoxycarbonyl azide were stirred together in 11. of 50% aqueous dioxane in the presence of 4 g. of magnesium oxide for 22 hours at 40°–45° C. The dioxane was distilled from the pale amber solution and to the residue, 500 ml. of water was added. On chilling, 58.7 . of solid separated, m.p. 141.5°–143.5° (after drying at 100° for 3 hours). Recrystallization of a sample of this material gave white crystals of m.p. 141°–141.5° C.

Microanalysis: C, 62.88; H, 7.83; N, 5.19.
Calc. for $C_{14}H_{20}NO_4$: C, 62.90; H, 7.92; N, 5.24.

EXAMPLE 15

Ethyl ester of 4-(2-t-butoxycarbonamidoethyl)phenoxy acetic acid 23.8 g. of the t-butoxyl ester of N-(4-hydroxyphenethyl) carbamic acid (0.1 mole) was dissolved in 250 ml. of hexamethylphosphoric triamide and to the stirred solution under nitrogen was added 2.4 g. of sodium hydride (0.1 mole) in small portions. The mixture was stirred until hydrogen evolution ceased (approx. 3 hours). To this stirred solution was added in a single portion 11.0 g. of ethyl bromacetate (0.102 moles) in 25 ml. of benzene. The external temperature rose from 7° to 19° C. The mixture was approximately neutral in 10 minutes. Water and ice (500 ml.) were added to the mixture, the slightly turbid mixture was extracted five times with 150-ml. portions of ether, the combined ether extracts washed with a few small portions of water and dried over magnesium sulfate. After removal of the drying agent, the solvent was distilled in the rotary evaporator. The residue, a pale amber syrup, weighed 30 g. 1 g. of this syrup was rubbed under 60°–90° petroeum ether whereupon it crystallized, m.p. 54.5°–56.5° C. After recrystallization from 60°–90° petroleum ether the m.p. was 55°–57° C.

Microanalysis: C, 63.37; H, 7.79; N, 4.58.

Calc. for $C_{17}H_{25}NO_5$: C, 63.14; H, 7.79; N, 4.33.

EXAMPLE 16

Ethyl ester of rac. -[2-(N-t-butoxycarbonamido)-1-hydroxyethyl]phenoxyacetic acid In the same manner as described in above in Example 5 there was obtained from 25.3 g. of the t-butyl ester of ac. N-(4,alpha-dihydroxyphenethyl) carbamic acid, 0.1 moles) 2.4 g. of sodium hydride (0.1 mole) in 350 ml. of hexamethylphosphoric triamide, treated with 7.0 g. of ethyl bromoacetate (0.1 mole) in 25 ml. of enzene, 31.7 g. of an amber syrup. A sample of this material was dissolved in hot carbon tetrachloride and on cooling crystals were deposited. These crystals melted at 56°–59° C; after drying in high vacuum at 45° C. the crystals were transformed to a colorless glass.

Microanalysis: C, 60.10; H, 7.32; N, 4.22.

Calc. for $C_{17}H_{25}NO_6$: C, 60.10; H, 7.42; N, 4.13.

EXAMPLE 17

Ethyl ester of rac. 4-[2-(N-t-butoxycarbonyl-N-methylamino)-1-hydroxyethyl]-phenoxyacetic acid In the same manner as described in Example 15 there was obtained from 26.7 g. of the t-butyl ester of rac. 1,alpha-dihydroxyphenethyl)-N-methyl carbamic acid, 0.1 mole) and 2.4 g. of sodium hydride (0.1 mole) in 250 ml. of hexamethylphosphoric triamide, treated with 7.0 g. of ethyl bromoacetate (0.1 mole) in 25 ml. of enzene, 39 g. of viscous syrup. Since repeated efforts to crystallize this product failed, it was hydrolyzed to the free acid as described below.

EXAMPLE 18

4-(2-t-Butoxycarbonamidoethyl)phenoxyacetic acid 29 g. of the above-described corresponding ethyl ester in Example 17 was suspended in 100 ml. of water : 80°–85° C., and the resulting suspension treated with 10% sodium hydroxide solution (drop by drop) until a permanent pH of 9–10 was obtained. To the cooled solution a 25% solution of acetic acid was added to pH whereupon a suspension of crystals was obtained. The solid was collected by means of seven successive treatments with 100 ml. portions of chloroform. The combined chloroform extracts were washed twice with 10 ml. portions of water, then dried. Distillation of the solvent in a rotary evaporator yielded 22.3 g. of a syrup that crystallized on standing. Recrystallization of this solid from 125 ml. of acetonitrile yielded 15.6 g. of slightly pinkish crystals of m.p. 110°–112.5° C. Another recrystallization from acetonitrile raised the m.p. to 12.5°–114° C.

Microanalysis: C, 61.03; H, 7.34; N, 4.63.

Calc. from $C_{15}H_{21}NO_5$; C, 61.00; H, 7.16; N, 4.74.

EXAMPLE 19 rac. -(2-t-Butoxycarbonamido-1-hydroxyethyl)phenoxyacetic acid

The above-described corresponding ethyl ester in xample 16 was hydrolyzed by suspending it in water 80°–85° C. and adding 10% sodium hydroxide solution until a permanent pH of 9–10 was obtained. After acidification with 20% citric acid solution to pH 3 the solution was extracted twice with 100 ml. portions of chloroform. The combined chloroform extracts were dried, the drying agent removed by filtration and the solvent distilled in the rotary evaporator. A pale amber syrup resulted. The syrup was dissolved in hot 60°–90° petroleum ether and on cooling, crystals separated. These off-color crystals, 22.55 g, were dissolved in 100 ml. of acetonitrile, treated with charcoal, filtered, and from the cooled filtrate 8.9 g. of solid, m.p. 98°–101° C. was obtained. After one more recrystallization from acetonitrile using decolorizing carbon 6.65 g. of slightly grayish crystals was obtained, m.p. 109°–111° C.

Microanalysis: C, 57.90; H, 6.88; N, 4.85.

Calc. for $C_{15}H_{21}NO_6$: C, 57.87; H, 6.80; N, 4.50.

EXAMPLE 20 rac. 4[2-N-t-Butoxycarbonyl-N-methylamino)-1-hydroxyethyl] phenoxyacetic acid

The corresponding ethyl ester of Example 17 was subjected to hydrolysis as described above in Examples 18 and 19. However, despite all attempts it was not possible to obtain the acid in crystalline form. It was therefore converted to the crystalline S-benzylthiuronium salt in the following manner: A weighed sample of the syrupy acid was treated with sufficient sodium hydroxide to form the sodium salt (pH 7.5–8). To this solution was added a concentrated solution of S-benzylthiuronium chloride, whereupon a precipitate formed. The solid was recovered, washed with cold water and then recrystallized from water to obtain white crystals of m.p. 163°–165° C. Analysis indicated that the crystals were the S-benzylthiuronium salt of the above-named acid.

Microanalysis: C, 58.64;, H, 6.77; N, 8.55.

Calc. for $C_{16}H_{22}NO_6 \cdot C_8H_{11}SN_2$: C, 58.60; H, 6.77; N, 8.60.

EXAMPLE 21

N-Hydroxysuccinimide ester of rac. 4-[2-N-t-butoxycarbonyl-N-methylamino)-1-hydroxyethyl]phenoxyacetic acid 3.25 g. (0.01 moles) of the syrupy acid described above in Example 20 was dissolved in 40 ml. of dimethoxyethane together with 1.15 g. of N-hydroxysuccinimide (0.01 moles) and to this solution was added 2.06 g. of dicyclohexylcarbodiimide (0.01 mole) whereupon the solution warmed preceptibly. The mixture was then stored at 5° C. for 21 hours. The dicyclohexylurea that had separated was removed by filtration, the filter cake washed with a little dimethoxyethane, and the combined filtrates distilled in the rotary evaporator. There remained 3.70 g. of a turbid syrup that was dissolved in 75 ml. of toluene and the undissolved dicyclohexylurea that had separated was removed by filtration. Distillation of the solvent left a syrup that was dissolved in 50 ml. of 2-propanol; 60°–90° petroleum ether was added to turbidity and the solution stored at 5° C. for 5 days. The crystals that separated were recovered, yield 2.5 g. of m.p. 106°–5° C.

Microanalysis: C, 56.58; H, 6.38; N, 6.73.

Calc. for $C_{20}H_{26}N_2O_2$: C, 56.87; H, 6.20; N, 6.63.

EXAMPLE 22

The N-hydroxysuccinimide ester of rac. 4[2-(N-t-butoxycarbonyl-N-methylamino)-1-hydroxyethyl]-phenoxy acetic acid was coupled to bovine serum album (BSA) following the procedure set forth below.

A total of 300 mg. (0.00447 mmoles) of bovine serum albumin (BSA) in 12 ml. of water treated with 6 ml. of a 0.5 M solution bicarbonate and then with 6 ml. of dimethoxyethane containing 60 mg. (0.075 mmoles) of the N-hydroxy-succinimide ester of rac. 4-[2-(N-t-butoxycarbonyl-N-methylamino)-1-hydroxyethyl]-phenoxy acetic acid. The mixture was stirred for 3 hours at room temperature , 96 ml. of ethanol was added and the solution evaporated to a small volume. The residue was then dialyzed against 200 volumes of water for 3 days with two changes per day and then the protected antigen was lyophillized. A second run was carried out under the same conditions as above with the exception that 162 mg. of the activated ester was employed.

Removal of the t-butoxycarbonyl protecting group was accomplished by stirring 50 mg. of the protected antigen with 50% trifluoroacetic acid in 50 ml. of methylene chloride for 1 hour at room temperature. The trifluoroacetic acid was then removed by flash evaporation. The residue was washed with water followed by evaporation. The residue was then taken up in water and lyophillized to yield the desired antigen.

Examination of the antigen produced from both runs using protein analysis and differential U.V. spectral analysis indicated that the antigen of run 1 contained 14 moles of hapten per mole (17% substitution based on 85 theoretically available amino groups) while the antigen of run 2 contained 25 moles of hapten per mole of BSA (29% substitution). This antigen is used to elicit antibody specific for epinephrine, metanephrine and synephrine. The antibody may be used in the assay of Example 14 using the radiolabeled compounds epinephrine $H^3$, synephrine $^{125}I$. and metanephrine $^{125}I$. The tritiated compound is commercially available and the iodinated labels are prepared using the standard chloramine T method well known in the art.

EXAMPLE 23

Rac. 4(2-t-butoxycarbonamido-1-hydroxyethyl)-phenoxy acetic acid was coupled to BSA utilizing the mixed anhydride method as follows.

A total of 39.46 mg. (0.1269 mmoles) of the protected hapten was added to 1 ml. of dry dioxane followed by the addition of 0.1269 mmoles of triethylamine in 0.5 ml. dioxane. The mixture was stirred at room temperature for 10 minutes and then cooled to 8° C. 0.1395 mmoles of isobutylchloroformate in 0.5 ml. dioxane was added and the solution was stirred for 20 minutes.

In a separate flask 100 mg. of BSA is dissolved in 10 ml. of water, the pH was adjusted to 9 with sodium hydroxide and 8 ml. of dioxane was added slowly with stirring. The solution was cooled to 8° C. and the protected hapten solution from above was added and stirred 30 minutes at 8° C. and then overnight at 4° C. at pH 9.

The solution was then treated with acid to neutrality, the solvent removed and the residue taken up in 5 ml. water (NaOH added to effect solution). Five milliliters of this solution was dialyzed successively against 6,000 ml. each of 0.5N NaOH, 0.1N NaOH, and $H_2O$ (2 times). The amine-blocked antigen solution was removed and lyophilized. The t-butoxycarbonyl group was removed with trifluoroacetic acid as described in Example 22.

Analysis of the resulting antigen by protein determination and U.V. analysis indicated that there were 64 moles of hapten per mole of BSA. The antigen so produced is useful in eliciting antibodies which recognize norepinephrine, normetanephrine and octopamine when injected into suitable animals. Such antibody may be incorporated in the assay of Example 14 using radiolabeled norepinephrine $^3H$, normetanephrine $^3H$ or $^{125}I$ and octopamine $^{125}I$. The labeled compounds are prepared as in Example 22.

EXAMPLE 24

The procedure of Example 23 was employed utilizing 4-(2-t-butoxycarbonamidoethyl)phenoxyacetic acid as hapten to produce an antigen containing 69 molecules of hapten per molecule of BSA. This antigen is useful in eliciting antibodies for dopamine and tyramine. The antibody may be used in the assay of Example 14 with dopamine $^3H$ and tyramine $^{125}I$, the source of which is as in Example 22.

EXAMPLE 25

N-[2-(4-hydroxyphenyl)ethyl]-2-[4-(2-aminopropyl)-phenoxy]acetamide

A. Into a 100 ml. flask equipped for stirring, with thermometer, and under nitrogen were placed 1.8 g. (5.8 × 10$^{-3}$ mole) of DL-3-[2-(t-butoxycarbamido)-propyl]phenoxyacetic acid, 45 ml. of dry tetrahydrofuran and 1.0 g (6.05 × 10$^{-3}$ mole) of carbonyl diimidazole. The mixture was stirred at room temperature (21° C.) for 2 hours when 0.63 g. (4.6 × 10$^{-3}$ mole) of tyramine was added. Stirring was continued at 21° C. overnight (ca. 18 hours). The mixture was then transferred to a separatory funnel and diluted with several volumes of ethyl acetate. The mixture was shaken with 3 portions of water. The organic phase was separated, dried over anhydrous sodium sulfate and evaporated at reduced pressure to give 2.6 g. of N-[2-(4-hydroxyphenyl)ethyl]-2-[4-t-butoxycarbonamidopropyl)-phenoxy]-acetamide, identified by nuclear magnetic resonance spectroscopy.

b. Into a 100 ml. flask equipped with thermometer, stirrer, and under nitrogen, were placed 1.97 g. of the product of step (a) and 28.4 ml. of trifluoroacetic acid. After stirring for 1 hour at room temperature (21° C.), the mixture was concentrated at 40° C. The residue was dissolved in 15 ml. of water and placed on a 15 mm × 150 mm column of ion exchange resin (IR-4B, acetate form) and eluted with water. Approximately 10 15 ml. fractions were collected, containing only the desired material. Evaporation of the combined fractions left a residue of 2.5 g. which was dissolved in water, neutralized by addition of solid sodium bicarbonate and stored in the refrigerator until precipitation was complete. After washing with cold water and crystallization, 0.4 g., m.p. 160°–163° C. was obtained. By further cooling, and concentrations additional product was obtained to total 0.52 g. of N-[2(4-hydroxyphenyl)ethyl]-2-[4-(2-aminopropyl)-phenoxy]acetamide.

Anal. Calcd. for $C_{19}H_{24}N_2O_3$; C, 69.49; H, 7.37; N, 8.53. Found: C, 69.41; H, 7.46; N, 8.40.

NMR spectrum: Compatible.

EXAMPLE 26

The N-[2-(4-hydroxyphenyl)ethyl]-2-[4-(2-aminopropyl)-phenoxy]acetamide was iodinated by procedures known per se employing Na $^{125}$I and chloramine-T to give N-[2-(4-hydroxyphenyl)ethyl]-2[4-(2-aminopropyl)-phenoxy]acetamide-$^{125}$I.

We claim:
1. N-[2-(4-hydroxyphenyl)ethyl]-2-[4-(2-aminopropyl)-phenoxy] acetamide.
2. N-[2-(4-hydroxyphenyl)ethyl]-2-[4-(2-aminopropyl)-phenoxy]acetamide-$^{125}$I.

* * * * *